United States Patent [19]
Reffner et al.

[11] Patent Number: 5,864,139
[45] Date of Patent: Jan. 26, 1999

[54] CONFOCAL MICROSPECTROMETER SYSTEM

[75] Inventors: John A. Reffner, Stamford; Steven H. Vogel, Shelton, both of Conn.

[73] Assignee: Spectra-Tech Inc., Shelton, Conn.

[21] Appl. No.: 800,930

[22] Filed: Feb. 13, 1997

[51] Int. Cl.[6] .......................... G02B 21/00; G01N 21/01; G01N 21/35

[52] U.S. Cl. ................. 250/339.07; 250/339.05; 250/347; 250/348; 250/353

[58] Field of Search .................. 250/339.01, 339.05, 250/339.06, 339.07, 339.08, 339.12, 347, 348, 353

[56] References Cited

U.S. PATENT DOCUMENTS

| | | |
|---|---|---|
| 4,843,242 | 6/1989 | Doyle . |
| 4,852,955 | 8/1989 | Doyle et al. ................... 250/339.08 X |
| 4,922,104 | 5/1990 | Eguchi et al. ................. 250/339.07 X |
| 5,160,826 | 11/1992 | Cohen et al. . |
| 5,581,085 | 12/1996 | Reffner et al. . |

FOREIGN PATENT DOCUMENTS 4-155247  5/1992  Japan ................................ 250/339.08
1826007  7/1993  U.S.S.R. ................................ 250/348

*Primary Examiner*—Edward J. Glick
*Attorney, Agent, or Firm*—Cohen, Pontani, Lieberman & Pavane

[57] ABSTRACT

A microscope for use in transmissive and reflective infrared spectral analysis of a sample positioned on a sample plane. The microscope uses a collimated beam for infinity correction. A collimated irradiating beam of infrared energy is input to the microscope and focused through a single confocal aperture whereupon the beam is re-collimated and provided to a focusing lens. The focusing lens focuses the beam on a subject sample which generates a resulting image beam. The resulting image beam is re-collimated and provided to an optical element which focuses the resulting image beam back through the single confocal aperture and to an infrared detector. In a preferred embodiment, the size of the single confocal aperture is adjustable and a dichroic element is included for providing simultaneous viewing and infrared measurement of a measured sample. Also in a preferred embodiment, a detector mounting apparatus is included for facilitating orientation of a detector at an infrared output of the microscope.

14 Claims, 9 Drawing Sheets

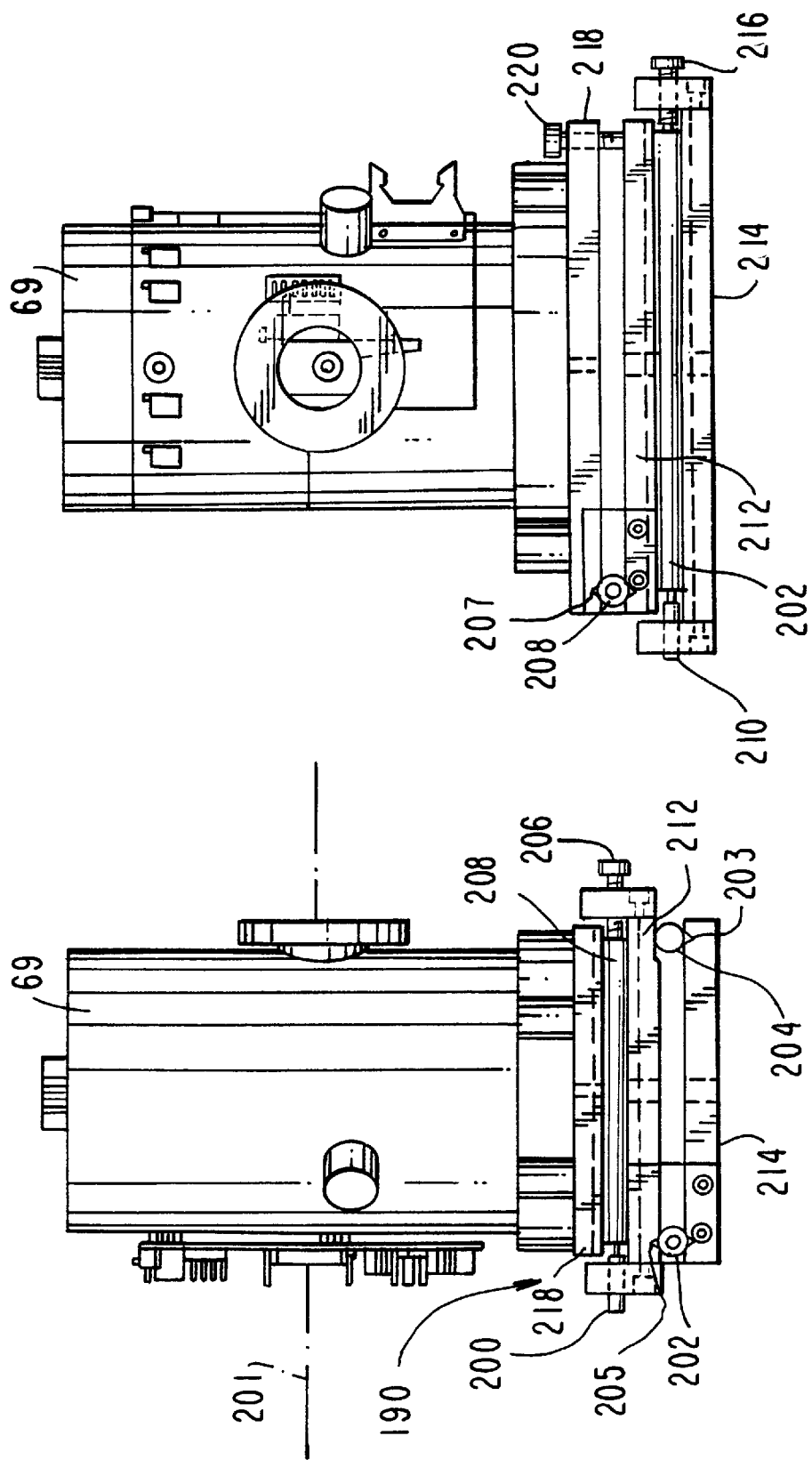

CONFOCAL MICROSPECTROMETER SYSTEM

BACKGROUND OF THE INVENTION

I. Field of the Invention

This invention generally relates to microscopy and spectroscopy. More particularly, the present invention pertains to a microscope for use in molecular microspectrometry using infrared radiant energy.

II. Description of the Related Art

The spatial resolution from conventional microscope-spectrometer combinations is limited by the relatively long wavelength ($\lambda$) of infrared radiation. For example, the diffraction limited spatial resolution (d) for a microscope with a limiting numerical aperture (N.A.) is $d=(0.62\lambda/N.A.)$. For analyzing molecular compounds such as organic substances, certain ionic salts and silicate minerals, radiant energy in the mid-infrared range of 2.5 to 25 $\mu m$ is most useful. In this mid-infrared spectral range, the conventional diffraction limited spatial resolution is about 10 $\mu m$.

In the field of light microscopy, there has been a steady progression away from fixed tube-length optical designs to infinity corrected microscopes. An infinity corrected microscope objective lens produces a nearly collimated beam of light from a sample. Viewing this collimated beam with a telescopic optical system produces a magnified image of the sample. Infinity corrected microscope optical designs have the advantage of allowing the placement of various optical elements in the collimated beam without degrading image quality.

Confocal apertures were first applied to infrared microspectroscopy by Messerschmidt and Sting to improve spatial resolution as is disclosed in U.S. Pat. No. 4,877,960. In this development, a pair of matched dual remote image plane masks or apertures were used to achieve the confocal geometry, as introduced by Minsky and explained in U.S. Pat. No. 3,013,467. On closer inspection, it was discovered that the separate masks or apertures were only required in a transmission mode for transmissive analysis. In a reflection mode for reflective analysis, however, use of a single aperture produces the confocal effect by defining both the area of the sample illuminated with radiant energy from the source, and the area of the sample reflecting radiant energy to the detector. The dual function of the sample defining aperture in reflection microspectrometry is common to several earlier designs.

For transmissive analysis with confocal sample defining masks, prior art systems require dual remote apertures having equal size images and the same geometrical shape at a sample plane. The infrared light used to radiate the transparent sample is masked twice; the first masking occurs before the light is incident to the surface of the sample such as when the light is travelling from a light source to the sample, and the second masking occurs after the radiant energy transmissively exits from the sample, i.e. when the light is travelling from the sample to a visible and/or infrared light detector.

The need for two separate apertures for transmission microspectrometry adds complexity and cost. For example, to properly operate such a system the user must align and match both the size and orientation of the two separate remote apertures as well as bring them both to a common focus. In addition, technical skills are required to adjust sample masks. As a result of the problems associated with dual remote aperture systems, many commercial microspectrometers have elected to employ single aperture systems for transmission measurements wherein the radiation signal travels through the aperture only once, i.e. in a direction from a radiation source to a sample, thus yielding simplicity of operation while sacrificing resolution.

Another drawback of existing microspectrometers is the inability to provide simultaneous visual observation of an object image while measuring or detecting the infrared light. For example, in many prior art systems, including the system described in commonly owned U.S. Pat. No. 5,581,085, a reflecting element (shown as element 24 in FIG. 1 of U.S. Pat. No. 5,581,085) must be removed from the path of the reflected or transmitted light so that the visible light is viewable by a user or a visible light detector, such as a video camera. When infrared measurements are needed, however, the reflecting element must be re-positioned in the light path of the irradiated sample so that the infrared light is reflected back to a detector. When so positioned, visible image observation is no longer available, thus making continuous automatic focusing features difficult, if not impossible, to implement.

A further drawback of prior art microspectrometer systems is that for an automated sequence of spectral measurements, the size or area of the dual apertures used to mask an object and to control the amount of light is fixed. Since the masked area of the sample cannot be varied during an automated spectral collection sequence, optimum sample masking is sacrificed. For example, if a sequence of particulates or cells were to be analyzed sequentially in an automated fashion, the prior art would require that the dual remote apertures be sized to the smallest feature and this size could not be changed during the sequence.

Still a further drawback of prior art microspectrometer systems is that they only accommodate and direct infrared light back to a single detector unit. If a different detector unit is desired, such as to obtain analyses other than those capable of being rendered by a first detector, the first detector must be disconnected or otherwise removed from an output light path and another detector substituted therefor.

Accordingly, it is an object of the present invention to provide a microscope using a single confocal aperture for transmission and reflection microspectrometry wherein during a transmission mode of operation, radiant energy passes through the aperture in a first and a second direction.

It is a further object of the present invention to provide a microscope having simultaneous visible image observation and infrared detection features so that an object image can be observed while infrared measurements are obtained and which provides a means for continuous adjustment of the sample focus by a focusing means.

It is still a further object of the present invention to provide a microscope having a mechanism for adjusting and regulating the area of a single confocal aperture to vary the radiated area of a subject sample.

It is another object of the present invention to provide a microscope accommodating multiple detectors and for selectively directing infrared light therebetween.

It is yet another object of the present invention to provide detector mounting platforms capable of three-dimensional movement for aligning a detector with an output infrared beam emanating from the microscope.

SUMMARY OF THE INVENTION

The present invention is partially based on the discovery that a single sample defining aperture can function as a confocal aperture for both transmissive and reflective microspectrometry. A microscope in accordance with the invention includes a single confocal aperture and a source of collimated infrared radiation for generating a collimated radiation beam. A first optical means directs the collimated radiation beam through the single confocal aperture and the second optical means receives and re-collimates the directed beam. In a transmission mode, a third optical means positioned for receiving the re-collimated beam focusses the re-collimated beam on a sample plane containing a transparent sample so that an area of the transparent sample is irradiated for generating an image beam. A fourth optical means is provided for receiving and collimating the image beam which is directed to a fifth optical means for focusing the collimated beam through the single confocal aperture for forming an output beam receivable by a detector.

In a preferred embodiment, a mechanism is provided for adjusting the size and orientation of the aperture, and a dichroic beam splitter is provided for allowing simultaneous viewing of the object image and infrared detection, thereby facilitating continuous automatic focusing of the visible and infrared beams on the sample plane. Also in the preferred embodiment, a mechanism, such as a moveable optical element, is provided for selectively directing the output infrared beam to one of a plurality of detectors.

In another preferred embodiment, a platform apparatus is provided upon which a detector is mounted. The platform apparatus facilitates three-dimensional movement of the detector to provide for proper alignment of the detector with the output infrared beam.

The various features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference numerals denote similar elements throughout the several views:

FIGS. 8A and 8B depict the detector mounting platform alignment mechanism in accordance with the present invention;

DETAILED DESCRIPTION OF THE PRESENTLY PREFERRED EMBODIMENTS

The inventive microspectrometer system of the present invention is designed for use with a Fourier Transform Infrared Spectrometer for performing visual examinations as well as external reflection and internal reflection spectral analyses of a sample. The microspectrometer system employs various standard optical components which are well known to those of ordinary skill in the art and which are more fully described in commonly owned U.S. Pat. No. 5,581,085, the entire contents of which are hereby incorporated by reference. For the sake of simplicity, the operation and function of such well known optical components will not be described herein.

This invention achieves the optical spatial resolution advantages of confocal microscopy using a single sample defining aperture for either transmissive or reflective spectral analysis and imaging. Employing a single sample aperture for confocal microspectrometry renders the inventive system easier to use and more precise and efficient relative to prior art systems because it alleviates the need for alignment and matching of dual remote apertures while reducing the cost of such systems.

Figure 1:
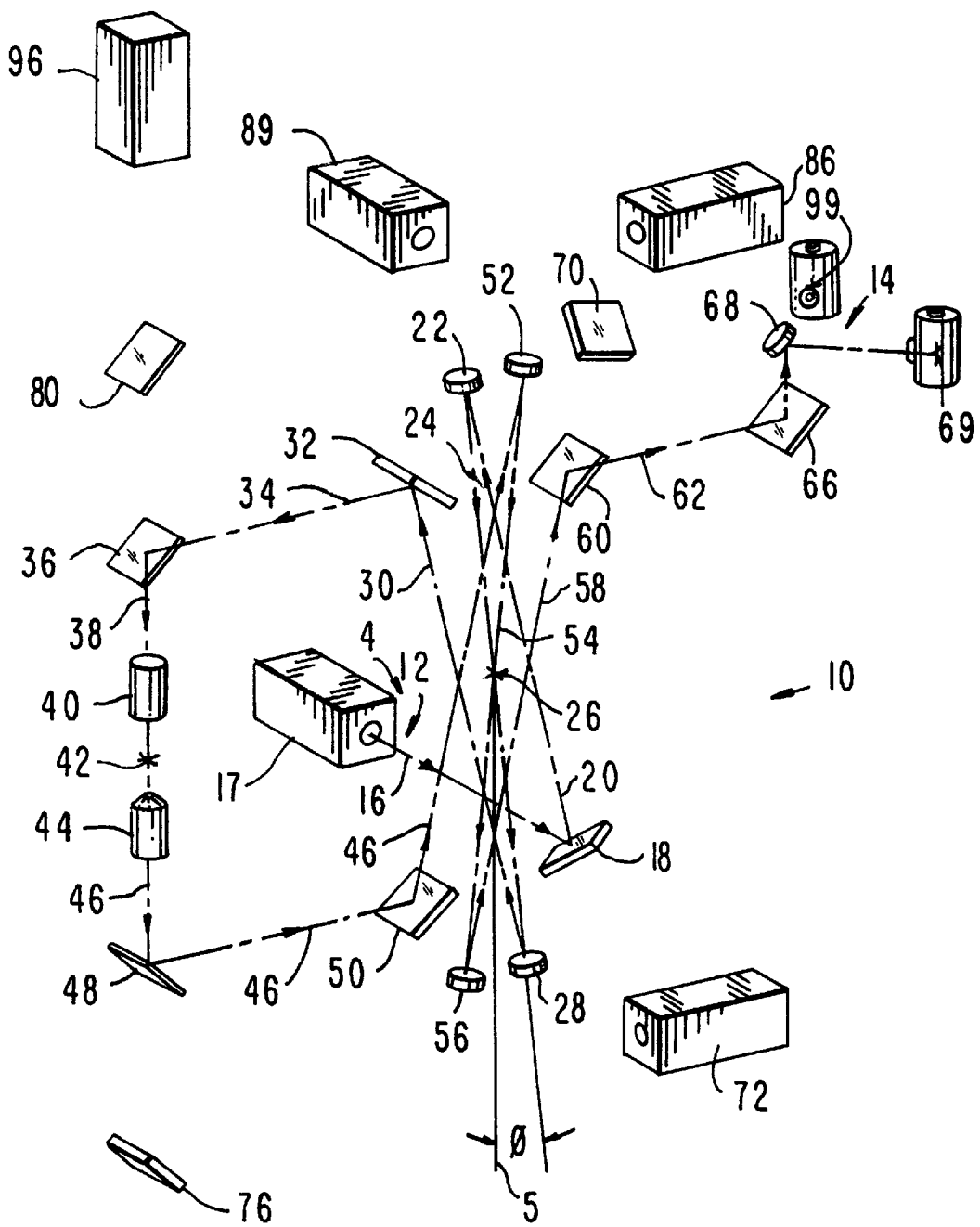
FIG. 1 is a perspective view of the optical elements defining the infrared light path in the transmission mode of a single aperture confocal microscope in accordance with the present invention.

With reference now to the drawings and initially to FIG. 1, a schematic representation of a single aperture confocal microspectrometer system 10 capable of operating in a transmission mode or a reflection mode is depicted. A description of the microscope operation in the transmission mode will now be given. Although not shown in the figures, the microspectrometer or microscope 10 includes a housing as is known by those of ordinary skill in the art and which is depicted in U.S. Pat. No. 5,581,085. The housing houses the various microscope components which are described herein.

Microscope 10 has an entry window 4 for receiving input optical signals. The entry window includes an input port 12 to which an input radiation or light signal window, such as a substantially collimated infrared beam 16 containing infrared wavelengths is applied. The collimated input infrared beam 16 may be generated, for example, from an infrared source 17, such as a Fourier Transform Infrared Spectrometer, as is known in the art.

The substantially collimated infrared input beam 16 is reflected by a reflective surface or flat mirror 18 toward a curved mirror 22. The reflected beam is shown as beam 20 and is received by a first optical means or curved mirror 22, which is preferably spherically shaped and which focusses the reflected beam 20 into a focused beam 24. Beam 24 is directed to a single remote aperture 26 which defines a conjugate field plane. Curved focusing mirror 22 is configured so that the first focused beam 24 forms an angle $\Phi$ relative to an axis 5—defined as a line perpendicular to and centered on the aperture plane. In a preferred embodiment, the angle $\Phi$ between the first focused beam 24 and the defined axis S is in the range of 5° to 15° and, most preferably, approximately 7°. It has been discovered that by inclining the focused beam 24 to the aperture 26, the same single aperture can be used as a dual confocal aperture for both transmission and reflection modes of microscope operation.

The remote confocal aperture 26 limits the cross-sectional area of the focus of beam 24. As is known by those having ordinary skill in the art, increased sample area definition is obtained by limiting the irradiated area of an object. This is known as a reduction of the Schwarzchild-Villiger effect and a reduction of the diffraction effect in infrared spectral measurements. As more fully explained below, the preferred embodiment includes an adjustable aperture 26 for further controlling the cross-sectional area of the focused beam 24, thereby controlling the irradiated object area.

After passing through aperture 26, focused beam 24 is directed to a second optical means or curved mirror 28, also preferably spherical, which re-collimates beam 24 into a collimated beam 30 which, in turn, is reflected by a reflective surface or flat mirror 32. In the preferred embodiment and as more fully described below, the reflected collimated beam (shown as beam 34) is directed to a reflective element 36 which is constructed from a dichroic material and functions as a dichroic beam splitter for directing an incoming beam into more than one path. Specifically, dichroic beam splitter 36 is constructed for passing certain wavelengths in a particular direction and for reflecting other wavelengths in another direction. A more detailed explanation of dichroic optical properties is found in U.S. Pat. No. 5,160,826.

Dichroic beam splitter 36 directs the reflected collimated beam 34 into an infinity corrected objective lens 40 which is described in more detail in U.S. Pat. No. 5,581,085. Lens 40 is constructed of mirror elements having appropriate curvatures and spacings therebetween so that the focusing properties of the lens bring the substantially collimated reflected beam 38 to a focus point. The focus point of lens 40 is at a sample plane 42 containing a sample material on which spectral analysis is to be performed.

In the transmission mode, the sample plane 42 contains a transparent sample (not shown) through which the beam 38—which is focused onto an area of the sample by objective lens 40—is directed for forming an image of the aperture onto the sample. The image beam exiting the sample is provided to a fourth optical means such as a condensing lens 44 which re-collimates the image beam and directs it to an optical element 48. The operation of the condensing lens 44 is known by those having ordinary skill in the art and may be a reflective lens or a refractive lens, although, a reflective lens is preferred.

In the preferred embodiment the focal length of the condensing lens 44 has the same focal length and magnification factor as the objective lens 40. To allow the single aperture to function as a dual confocal aperture, the magnification factors must be substantially equal for the incident and transmitted beams at the sample plane 42 and the conjugate field aperture plane containing aperture 26.

The condensing lens 44 produces a substantially collimated beam 46 which is a re-collimated beam of the image beam produced by irradiating an area of the sample object contained on the sample plane 42. The re-collimated beam 46 is reflected by a reflective element 48 which, like reflective element 36, is also constructed of a dichroic material and functions as a beam splitter for directing various beams provided thereto to different paths. The reflected collimated beam is provided to a reflective surface 50 which is preferably a flat mirror for directing beam 46 to a fifth optical means which is a curved focusing mirror 52. Like mirror 22, focusing mirror 52 is spherically shaped and focuses the collimated beam 46 back through the single remote aperture 26 as a focused beam 54. In other words, the infrared radiation beam 46 passes through the same single aperture 26 for a second time during which the cross-sectional area of the radiation beam is again limited, thus further improving the sample definition of the resulting image.

The resulting beam 54 is directed to another curved spherical mirror 56 which re-collimates the focused beam 54, shown as collimated image beam 58, and directs it to an output terminal 14 of the microscope 10. Specifically, beam 58 is directed to a reflective element 60 for reflecting the re-collimated image beam 58 into a beam 62 which is directed to a reflective surface such as a mirror 66 for providing the reflected infrared output beam to the optical element 68. Optical element 68 focuses the re-collimated beam 62 on an infrared radiant energy detector 69. The signal generated by the infrared radiant energy detector is passed to a Fourier Transform spectrometer for signal processing.

As explained more fully below, reflective element 60 may be a dichroic beam splitter which accommodates the introduction of visible light into microscope 10 for use in an illumination mode. Furthermore, optical element 68 may be moveable, as is preferred, for directing the reflected beam to a plurality of detectors 69 and 99 for obtaining a variety of spectral analyses. In other words, by changing the orientation of optical element 68, the resulting output beam can be directed to one of a plurality of appropriately placed detectors to obtain a variety of measurements.

Figure 2:
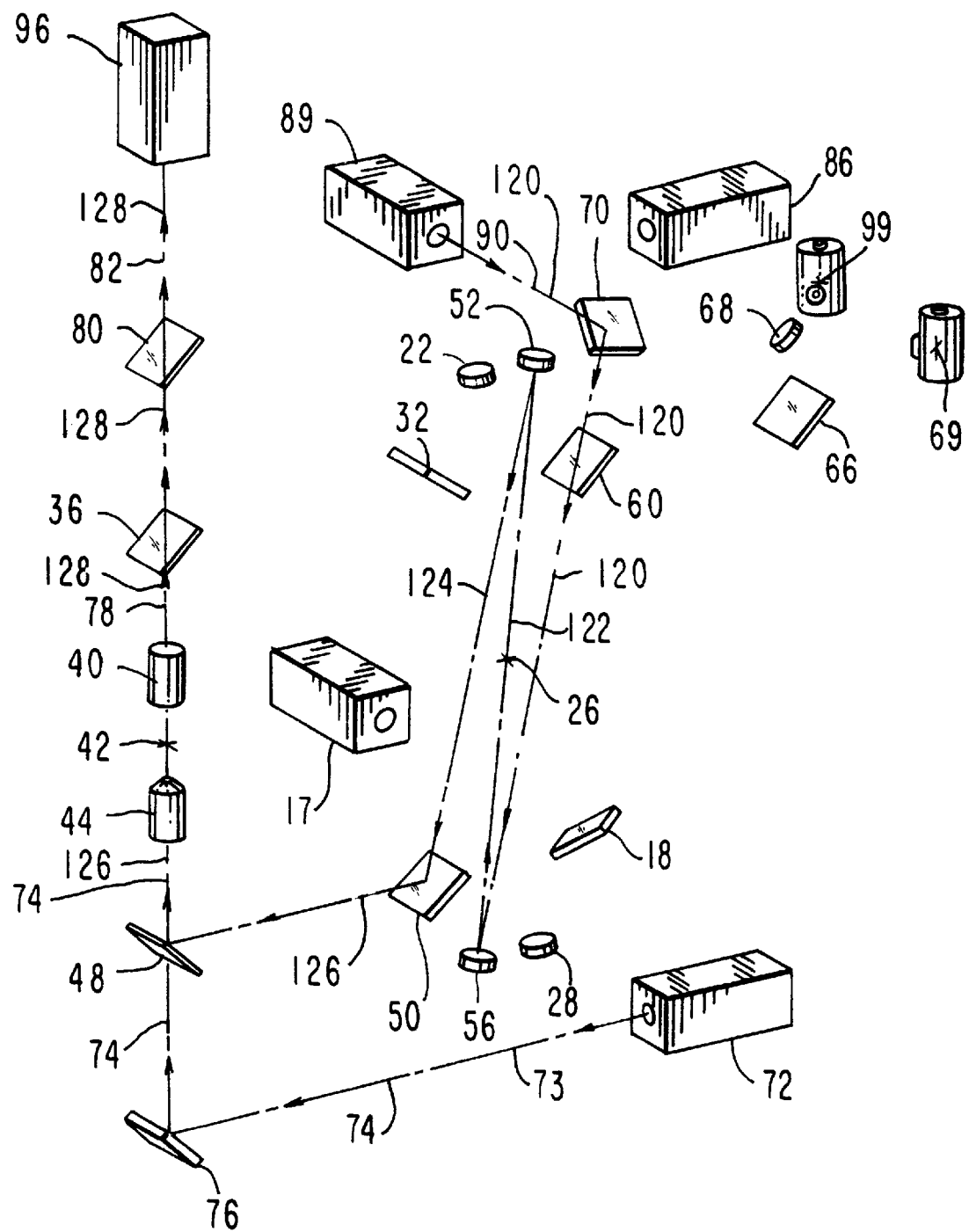
FIG. 2 is a perspective view of the optical elements defining the visible light path in the transmission mode of the microscope system of FIG. 1.

The microscope 10 is capable of simultaneously operating in an illumination mode which allows a user to view a sample positioned on sample plane 42 which is illuminated by both visible light and infrared radiation. With reference now to FIG. 2, an illumination mode for illuminating a sample during transmissive analysis will now be described. As shown, the microscope 10 contains several visible light sources 72, 86 and 89 positioned for illuminating sample plane 42 either through top illumination via objective lens 40, or through bottom illumination via condensing lens 44. For transmission mode illumination, bottom illumination of the sample plane 42 through lens 44 is used. The various visible light beams are shown in the dashed-lines in FIG. 2.

With continued reference to FIG. 2, a first transmission illumination mode is generated by visible light source 72 which generates and directs a visible illuminating beam 74 through a visible beam input port 73 and at a reflection surface such as flat mirror 76. Mirror 76 directs the reflected beam 74 through the dichroic element 48 and into condensing lens 44 which focuses beam 74 on the sample plane 42. The image beam exiting the sample plane 42 is re-collimated by objective lens 40 to form a collimated beam 78. The collimated beam 78 is then provided to dichroic element 36 which passes beam 78 to visible beam splitter 80. Beam splitter 80 provides the substantially collimated visible image beam (shown as beam 82) to a viewing mechanism 96 such as, for example, an eyepiece or video camera, for forming an image from beam 82.

A second transmission illumination mode is created by visible light source 89. The second mode uses visible light to illuminate the sample object area that is irradiated by the infrared beam 16. To accomplish this, visible light having a beamwidth substantially equal to the beamwidth of the infrared beam 16 (shown in FIG. 1) is input to the microscope entry window 4, either through input port 12 (shown in FIG. 1) or through a separate visible light input port 90 and is directed to the sample plane 42 substantially along the same path that is followed by the infrared radiation beam, i.e. coaxial with the infrared beam. Accordingly, a collimated visible beam 120 generated by visible light source 89 is input to port 12 or port 90. If port 12 is used, it is necessary to replace flat mirror 18 with a dichroic element for accommodating both infrared beam 16 and visible beam 20. If port 90 is used, as is shown in FIG. 2, beam 120 is directed at flat mirror 70 which reflects beam 120 to the curved mirror 56. As is known in the art, curved mirror 56 focuses a collimated beam travelling in one direction and collimates a focused beam travelling in another direction. In other words, curved mirror 56 not only converts the focused infrared beam 54 into the collimated beam 58 (shown in FIG. 1), but it also focuses the collimated visible light beam 120 into a focused visible light beam 122 which, as shown, is directed through aperture 26 and received by curved mirror 52. Likewise, curved mirror 52 focuses collimated infrared beam 46 through aperture 26 as a focused beam 54 (also shown in FIG. 1), and also re-collimates the focused visible beam 122 into a collimated beam 124. The collimated visible beam 124 is reflected by reflective surface or mirror 50 as reflected collimated beam 126 which is further reflected by dichroic element 48 and focused on sample plane 42 by lens 44 to form a visible image of the sample plane. The collimated visible beam (shown as beam 128) is then received by the viewing mechanism 96 for forming a visible image of the sample area. As should be readily apparent, both lenses 40 and 44 operate on both visible beams 74 and 126 generated from visible beam sources 72 and 89, respectively.

As explained above, the operation of the dichroic material beam splitters is such that certain wavelengths contained in an incoming beam will be directed in one direction while other wavelengths are directed in another direction. For example, beam splitter 36 will reflect beam 34 into lens 40 (shown in FIG. 1) while passing beam 128 (i.e. the visible wavelengths formed from irradiating the sample plane with visible light) to visible beam splitter 80. The resulting beam can then be provided to a video camera connected to a computer which, in turn, is connected to a focusing apparatus on either or both of lenses 40, 44 and/or sample plane 42, to facilitate continuous automatic focusing of the lenses or sample plane without the need for removal of reflective surface 36 to obtain the visible image.

Figure 3:
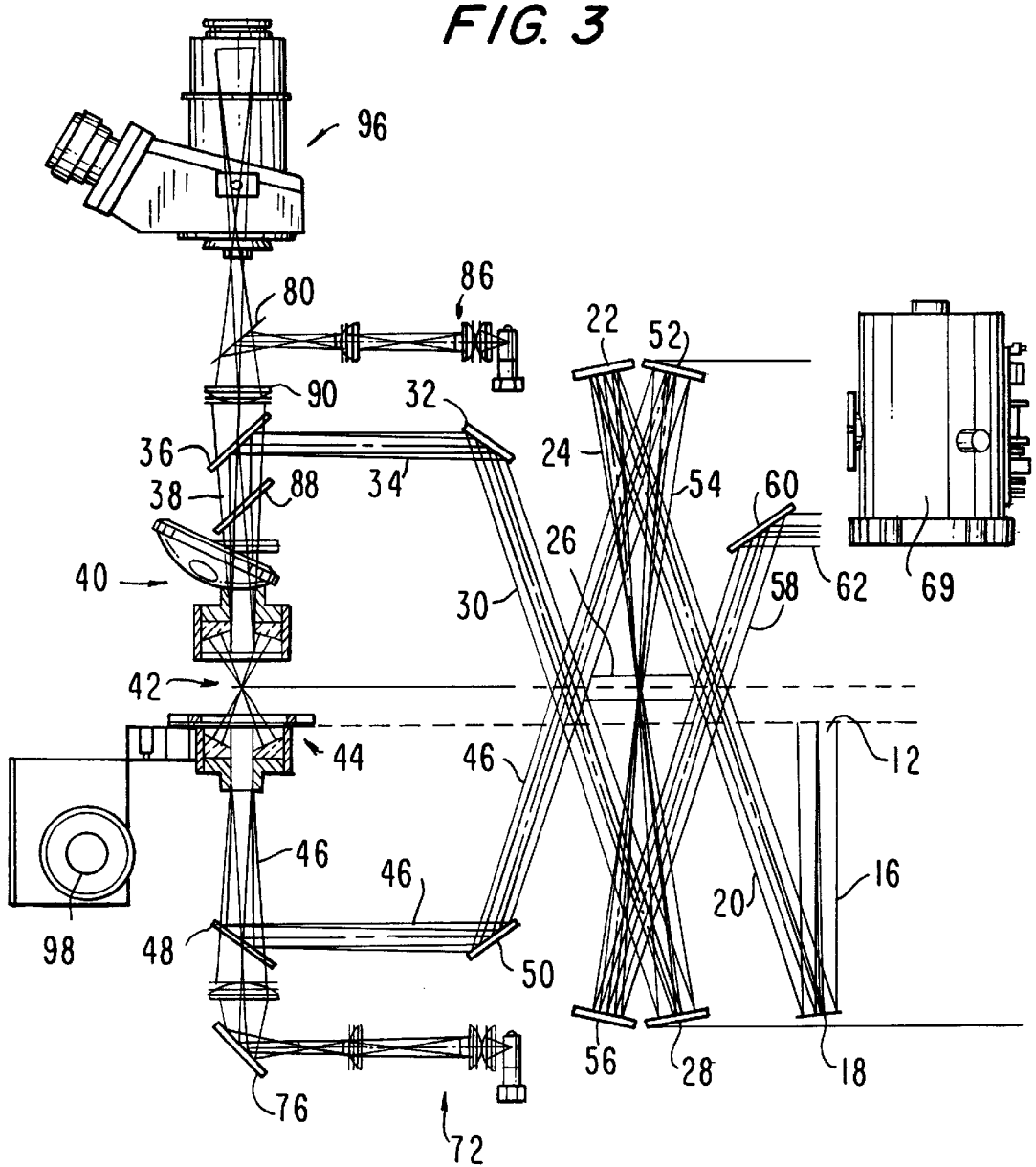
FIG. 3 is a partially elevational, partially schematic view depicting the infrared beam path in the transmission mode, the visible transmission and reflection beam paths and the focus control means of the single aperture confocal microscope of the present invention.

With reference now to FIG. 3, another view of the infrared and visible beam paths of the microscope 10 in the transmission mode is shown. The system shown in FIG. 3 is similar to the system shown in FIG. 1 except that it contains several additional elements. For example, a differential interference contrast (DIC) optical component 88 is preferably included between the dichroic element 36 and the objective lens 40 for improving the visible image contrast of the sample positioned on the sample plane 42, as is known in the art. The visible image is passed by visible beam splitter 80 and provided to the viewing mechanism 96 which, as stated above, may be a direct viewing means, such as a monocular, binocular or trinocular viewer, video camera, television, etc., for obtaining a visible image of the illuminated sample.

As explained above, the dichroic element 36 provides for simultaneous viewing and spectral analysis of a sample because it simultaneously reflects the incoming infrared beam 34 to objective lens 40 and, eventually to an infrared detector 69 while providing the visible image to the viewing mechanism 96. Accordingly, by providing a focusing motor 98 controlled by the viewing mechanism 96 and connected to the objective lens 40 and/or to the condenser lens 44 and/or to the sample plane 42 on which a subject sample is placed, continuous automatic focusing can be obtained. For example, if the visible image is blurry or otherwise out of focus, the viewing mechanism 96 will send a signal to the focusing motor 98 to re-focus or otherwise adjust the objective and/or condenser lenses and/or sample plane.

Figure 4:
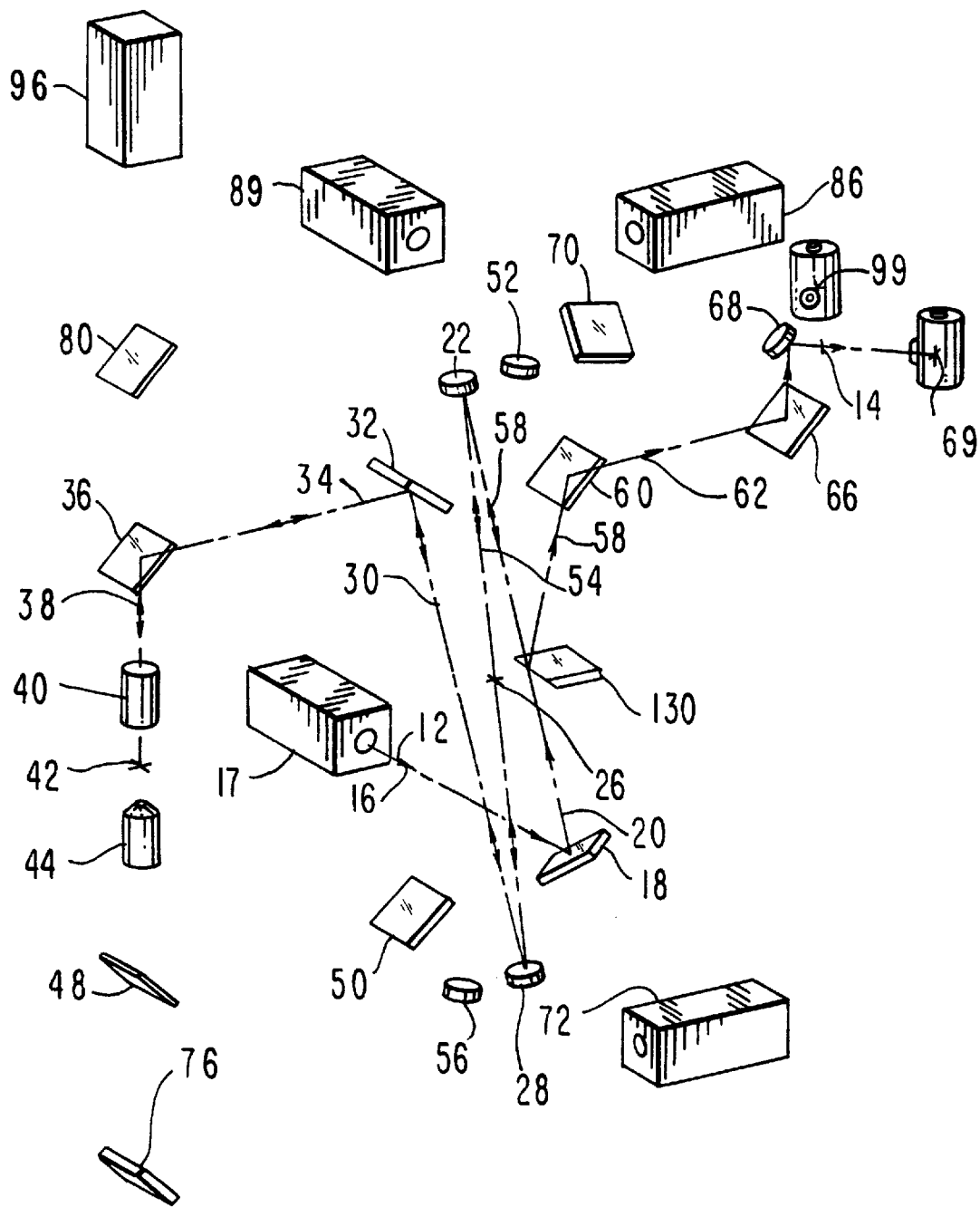
FIG. 4 is a perspective view of the optical elements defining the infrared light path in the reflection mode of the single aperture confocal microscope in accordance with the present invention.
Figure 5:
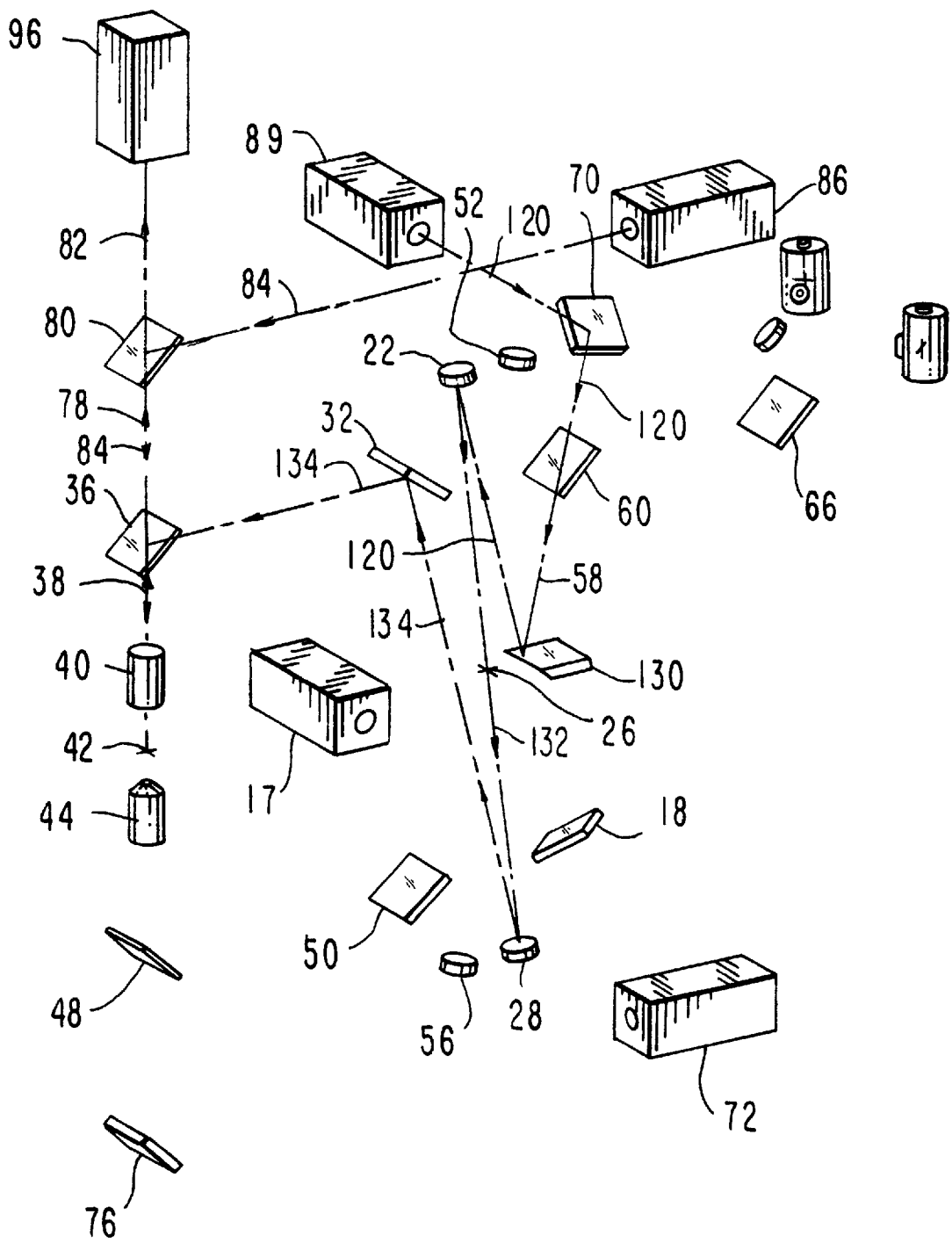
FIG. 5 is a perspective view of the optical elements defining the visible light path in the reflection mode of the microscope system of FIG. 4.

Referring now to FIGS. 4 and 5, the infrared reflection mode operation of the microscope 10 will now be described. As shown in FIG. 4 the infrared radiation beam 16 generated by an infrared source 17 traverses substantially the same path toward the sample plane 42, (i.e. from infrared source 17 to sample plane 42), as the path traversed away from sample plane 42, (i.e. from sample plane 42 to the optical element 68). Specifically, the collimated infrared radiation beam 16 is directed to the first flat mirror 18 which reflects the beam (shown as beam 20) toward a beam splitter 130 having a tapered end and a reflective upper surface. Beam splitter 130 blocks substantially half of beam 20 while passing the remainder to the curved mirror 22 for focusing through aperture 26. The resulting beam is re-collimated by spherical mirror 28 for forming a collimated infrared beam 30 which is directed to reflective surface 32. Reflective surface 32 reflects the collimated infrared beam 30 (shown as beam 34) toward dichroic element 36 which, in turn, reflects the beam to lens 40 for focusing on the sample plane 42.

For reflection mode operation, a reflective non-transparent sample is positioned on sample plane 42 which reflects the focused beam back through lens 40. Lens 40 collimates the reflected beam (shown as collimated beam 38) toward dichroic element 36 for reflection towards reflective surface 32 and to curved mirror 28. Curved mirror 28 then re-focuses the reflected beam back through aperture 26 toward curved mirror 22 which re-collimates the focused beam into collimated beam 58. Beam 58 is directed back toward beam splitter 130 and, specifically, to the reflective upper surface thereof. Beam splitter 130 reflects the collimated beam 58 to reflective dichroic element 60 for receipt by optical element 68. As explained above, optical element 68 is moveable for selectively directing the output infrared beam to one of the infrared detectors 69 or 99.

With reference now to FIG. 5, the visible light paths during the reflection mode are depicted. Like the illumination transmission modes described hereinabove wherein a first illumination mode is used for visually illuminating the sample plane 42 and a second illumination mode is used for visually illuminating the infrared irradiated sample object area, the reflection mode also uses two illumination modes for these purposes. The first mode is used for illuminating the sample plane 42 by generating, from visible light source 86, a visible light beam 84. Beam 84 is directed to visible beam splitter 80 which, in turn, reflects the visible beam to dichroic beam splitter 36 which passes beam 84 to lens 40 for focusing on sample plane 42. As a sample object positioned on sample plane 42 in the reflection mode is non-transparent, the visible light is reflected back from the sample to beam splitters 36 and 80 for receipt by the viewing mechanism 96.

The second reflection illumination mode uses visible light source 89 to produce a collimated visible beam 120 which is directed at mirror 70. The collimated visible beam is reflected to the upper surface of beam splitter 130 which, as described above, has a reflective material disposed thereon, and which further reflects beam 120 to curved mirror 22. Mirror 22 focuses the collimated reflective beam 120 on aperture 26 which passes a focused visible beam 132 that is received by curved mirror 28. Mirror 28 re-collimates focused beam 132 into beam 134 which is directed at reflective surface 32, toward dichroic element 36 and downward to objective lens 40 for focusing on sample plane 42.

The visible light is reflected off of the sample plane 42 to viewing mechanism 96. In other words, the reflected visible light will be passed by dichroic beam splitter 36 and visible beam splitter 80 and provided to viewing mechanism 96. As should be appreciated, by directing the visible light through the same aperture 26 as the infrared light, the area of the sample object positioned on sample plane 42 that is irradiated by the infrared beam, either in the reflection or transmission modes, is the same area that is illuminated by the visible light. This allows for viewing of the irradiated area.

Figure 6A:
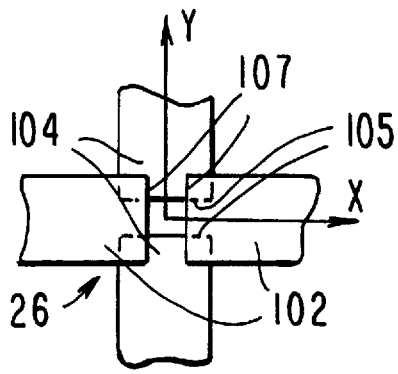
FIGS. 6A–6C depict the aperture of the present invention in different opening positions.

With reference now to FIGS. 6A–6D, the adjustment of the single confocal aperture 26 will now be described. As explained above, the aperture limits the cross-sectional area of the incoming infrared beam (i.e. the beam travelling from the beam source 17 to the sample plane 42) and also limits the cross-sectional area of the resulting image beam (i.e. the beam 46 travelling from sample plane 42 to the optical element 68) as shown in FIG. 1. As explained above, the size of the aperture and, hence, the width of the beam passing through the aperture, can be adjusted. Aperture 26, which is shown in FIG. 6A positioned on X-Y axes, is rotatable about the origin and includes two pairs of opposing shutters 102 and 104. Shutter pair 104 is shown having opposing edges 105 positioned parallel to the X axis and shutter pair 102 is shown having opposing edges 107 positioned parallel to the Y axis. The shutter pairs can be adjusted, as described more fully below, to vary the aperture size.

Figure 6B:
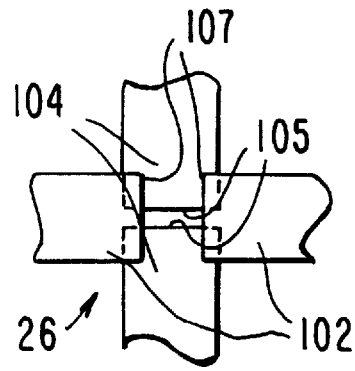
Figure 6C:
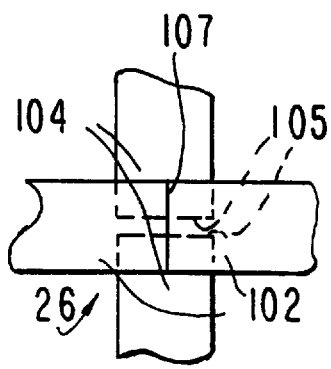

FIG. 6A depicts a substantially square-shaped aperture wherein the distances between edge pairs 105 and 107 are equal, and FIG. 6B depicts a rectangular-shaped aperture wherein the distance between edges 105 is less than the distance between edges 107. In FIG. 6C, the aperture 26 is shown in a closed position wherein edges 107 are in contact with each other. It should be recognized that aperture 26 can, likewise, be closed by bringing edges 105 together instead of edges 107.

Figure 6D:
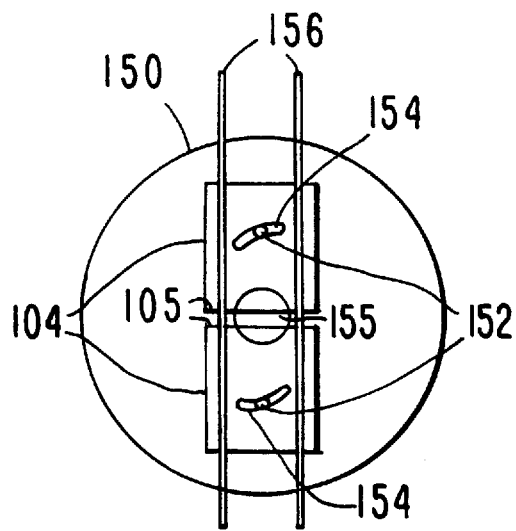
FIG. 6D depicts the aperture size adjustment mechanism of the present invention.

With reference to FIG. 6D, the shutter pairs are operated by a cam mechanism which, when turned in a particular direction, opens and closes the shutter pairs. Specifically, the cam mechanism includes a pair of washers or disks 150 (only one of which is shown in the figure) having a central opening 155. Shutter pair 104 is linked to washer 150 via pins 152 connected at one end to the washer, with the other end seated in curved slots 154 formed in shutters 104. A pair of substantially parallel rods 156 is connected to shutters 104 and insure that the shutters remain aligned with each other. Rotation of washer 150 causes shutters 104 to move in a translational direction parallel to rods 156. A similar configuration exists for shutter pair 102 which is mounted to a washer (not shown) similar to washer 150 but angularly displaced therefrom by 90°. As can be appreciated, by selectively adjusting the size of aperture 26, the area of the subject sample to be irradiated can be adjusted.

Figure 7A:
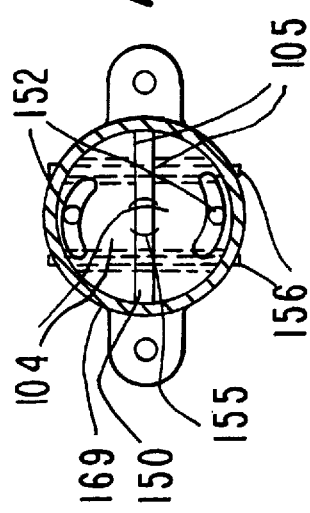
FIGS. 7A–7C depict the rotating apparatus of the aperture size adjustment mechanism of FIG. 6D.
Figure 7B:
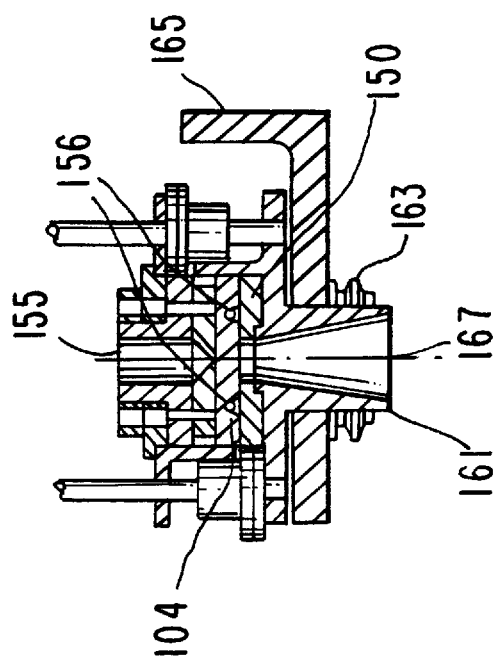
Figure 7C:
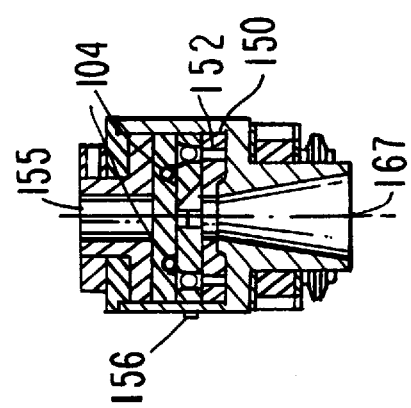

As explained above, the aperture size is adjusted by moving the shutter pairs 102 and 104. In addition to size adjustment, the aperture is also rotatable about an axis. For example, and with reference now to FIGS. 7A–7C, the washer 150 is shown positioned about an axis 167. A frame 169 is provided to which rods 156 are secured. Frame 169 is connected to a support bracket 165 which is fixedly mounted to the microscope housing and which has a central bore defined therein. A collar member 161 is rotationally mounted in the central bore as shown and has a belt-driven pulley or gear 163 fixedly secured to the collar member. The belt-driven pulley 163 is rotatably driven by a belt (not shown) connected to a motor (not shown). When pulley 163 is rotated, the frame 169—to which shutter pairs 102 and 104 are secured—is also rotated, thereby causing angular displacement of aperture 26.

With reference now to FIGS. 8A and 8B, a detector alignment mechanism 190 of the present invention will now be described. FIG. 8A depicts detector 69 having a detector axis 201 and mounted on the alignment mechanism 190 so that the detector axis extends from left to right in the figure, whereas FIG. 8B shows the detector of FIG. 8A rotated by 90°. The alignment mechanism includes a base plate 214 which is separated from a middle plate 212 by pairs of rods 202 and 204. Base plate 214 has a notch or groove 203 formed therein along an edge in which rod 204 is fixedly secured, and middle plate 212 has a notch 205 in which rod 202 is fixedly secured. The edges of rod 202 are secured to base plate 214 by a spring plunger 210 at one end and a thumb screw 216 at the other end. Adjustment of the screw 216 causes linear movement of middle plate 212 relative to base plate 214 (i.e. movement in a direction perpendicular to axis 201).

The mounting mechanism also includes a top plate 218 spatially positioned from middle plate 212 by a rod 208 and a screw 220. Rod 208 is seated in a groove 207 formed in plate 218 and affixed thereto. Rod 208 is also supported at its ends by a spring plunger 200 and a thumb screw 206. Adjustment of the thumb screw 206 causes linear movement of plate 218 relative to middle plate 212 and base plate 214 (i.e. movement in a direction parallel to axis 201). Additional movement of plate 218 is caused by adjusting screw 220 which moves an edge of plate 218 upward and downward relative to plate 212. As can be appreciated, the mounting mechanism provides for three types of motion of the detector 69, which, in turn, provides for easy alignment of the detector to receive the resulting infrared beam.

Figure 9A:
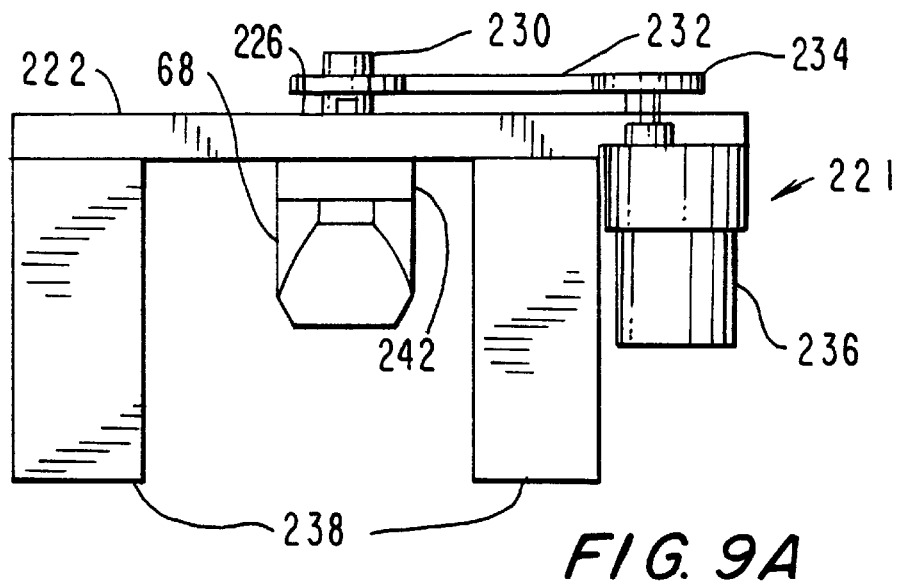
FIG. 9A is a front elevational view of the infrared light directing mechanism for accommodating multiple detectors in accordance with the present invention.

As explained above, the inventive microspectrometer system provides for the detection of infrared radiation by multiple detectors by selectively directing an output infrared beam thereto. With reference now to FIG. 9A, this is accomplished by connecting optical element 68 to an infrared light directing mechanism 221. The infrared light directing mechanism 221 contains a platform 222 which is supported by a pair of supports 238. The optical element 68 is rotatably connected to the platform 222 along with an optic mount 242, a stop block 226 and gears 230, 234. A belt 232 driven by a motor 236 connects gears 230 and 234 together. When motor 236 is activated, gear 234 is rotated which, in turn, moves belt 232 and gear 230. When gear 230 is moved, optical element 68 which is connected thereto, moves between a first position and a second position which are defined by the stop block 226 and which are, preferably, 180° apart.

Figure 9B:
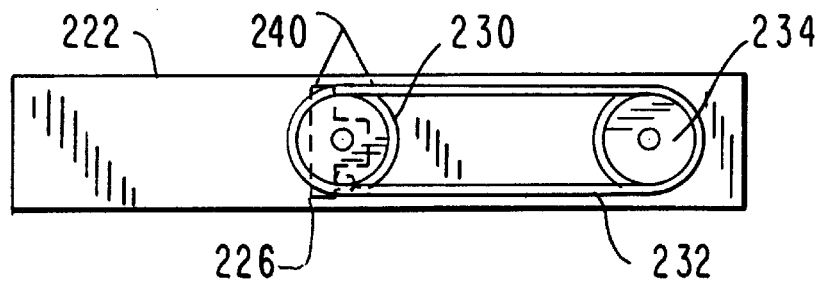
FIGS. 9B and 9C are top planar views of the mechanism depicted in FIG. 9A.
Figure 9C:
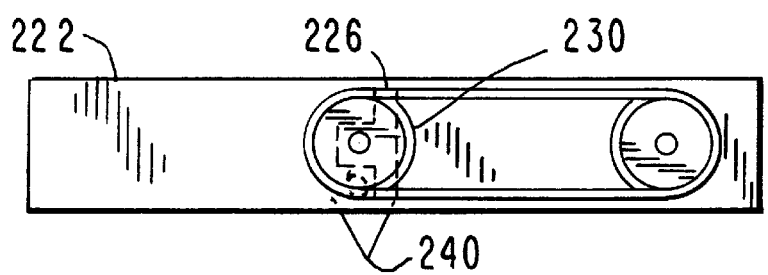

The two positions of the optical element 68 are shown in FIGS. 9B and 9C. Specifically, in FIG. 9B the optical element 68 having a focus point 240 is shown oriented in the first position (i.e. in an upward position), and in FIG. 9C the focus point 240 is in the second position (i.e. in a downward position). Thus, as shown in FIGS. 9A–9C, movement of belt 232 causes focus point 240 to move between two positions such that, when a detector is placed on either side of platform 222, an output infrared beam received by optical element 68 can be selectively directed to either detector. Although only two positions are shown, it will be readily understood by those having ordinary skill in the art that more positions can be defined for accommodating multiple detectors.

Thus, while there has been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. It is the intention, therefore, to be limited only as indicated by the scope of the claims appended hereto.

We claim:

1. A microscope for providing transmissive spectrometry by irradiating a substantially transparent sample with a beam of energy, said microscope comprising:

an input port for receiving a beam of infrared radiation;

a single remote aperture;

a first optical means for focusing the infrared radiation beam at said single remote aperture and for directing said focused radiation beam through said single remote aperture;

a second optical means for receiving and collimating the focused beam;

a third optical means for receiving the collimated beam and for focusing the collimated beam on a sample plane containing a transparent sample, so that an area of the substantially transparent sample is irradiated by the focused beam for generating a resulting image beam;

a fourth optical means for receiving and collimating the resulting image beam; and a fifth optical means for focusing the resulting image beam which was collimated by said fourth optical means at said single remote aperture and for directing said focused resulting image beam through said single remote aperture for forming an output image beam capable of being received by a detector means.

2. The microscope of claim 1, wherein said single remote aperture is contained on a plane defining an axis and wherein said focused radiation beam passes through said single remote aperture at an angle within the range of 5° to 15° relative to said axis.

3. The microscope of claim 2, wherein the resulting image beam passes through said single remote aperture at an angle within the range of 5° to 15° relative to said axis.

4. The microscope of claim 3, further comprising a dichroic beam splitter positioned between said fourth optical means and said fifth optical means, said beam splitter configured for directing infrared radiation toward said fifth optical means and for passing non-infrared radiation toward said fourth optical means.

5. The microscope of claim 1, further comprising a dichroic beam splitter positioned between said second optical means and said third optical means, said beam splitter being configured for directing infrared radiation toward said third optical means and for passing non-infrared radiation from said sample plane to a viewing mechanism.

6. The microscope of claim 5, wherein said viewing mechanism further comprises an image detector which receives the non-infrared radiation from said dichroic beam splitter, and a focusing mechanism controllable by said image detector when said image detector determines that an image generated by irradiating the transparent sample with the focused beam is not in focus.

7. The microscope of claim 6, further comprising a differential interference optical component positioned between said dichroic beam splitter and said third optical means for improving the image of the substantially transparent sample received by said image detector.

8. The microscope of claim 1, further comprising an aperture adjustment mechanism for adjusting the size of said single remote aperture for controlling the area of said focused radiation beam and for controlling the area of the resulting image beam, for regulating the irradiated area of the transparent sample.

9. The microscope of claim 8, wherein said aperture adjustment mechanism rotates said single remote aperture.

10. The microscope of claim 8, wherein said aperture adjustment mechanism comprises first and second pairs of spaced shutters, each pair having opposing edges, said shutter pairs being angularly offset from each other, and wherein the size of said remote aperture is adjusted by varying the spacing between said opposing edges of said shutter pairs.

11. The microscope of claim 1, wherein said focused radiation beam is directed through said single remote aperture in a first direction and wherein the resulting image beam is directed through said single remote aperture in a second direction.

12. The microscope of claim 1, wherein the detector means includes at least one detector and further comprising an optical element for receiving the output image beam and directing the output image beam to the at least one detector.

13. The microscope of claim 12, wherein the detector means includes a plurality of detectors and the optical element is moveable for selectively directing the output image beam to one of the plurality of detectors.

14. The microscope of claim 1, further comprising a detector alignment mechanism for supporting said detector means in a position for receiving said output image beam, said detector adjustment mechanism comprising means for adjusting the three-dimensional position of the detector means relative to said output image beam.

* * * * *